United States Patent
Chang et al.

(10) Patent No.: US 8,545,684 B2
(45) Date of Patent: Oct. 1, 2013

(54) SENSING ELEMENT AND METHOD OF MAKING THE SAME

(75) Inventors: Fenglian Chang, Grand Blanc, MI (US); Kerry J. Kruske, Oakey, MI (US); Rick D. Kerr, Fenton, MI (US)

(73) Assignee: Delphi Technologies, Inc., Troy, MI (US)

( * ) Notice: Subject to any disclaimer, the term of this patent is extended or adjusted under 35 U.S.C. 154(b) by 266 days.

(21) Appl. No.: 12/899,919

(22) Filed: Oct. 7, 2010

(65) Prior Publication Data

US 2011/0020535 A1    Jan. 27, 2011

Related U.S. Application Data

(62) Division of application No. 11/281,056, filed on Nov. 16, 2005, now abandoned.

(51) Int. Cl.
*B05D 5/12* (2006.01)
*G01N 9/00* (2006.01)

(52) U.S. Cl.
USPC .......... 204/424; 73/23.31; 73/23.32; 427/77; 75/235; 252/514; 419/23; 419/20; 204/290.08

(58) Field of Classification Search
USPC .............. 156/89.12; 219/552, 592; 204/400, 204/421–429, 290.08; 427/77; 205/781, 205/783.5–785; 73/23.31, 23.32; 419/23, 419/20; 75/235; 252/514
See application file for complete search history.

(56) References Cited

U.S. PATENT DOCUMENTS

| | | | |
|---|---|---|---|
| 4,283,441 A | 8/1981 | Haecker et al. | |
| 5,338,708 A | 8/1994 | Felten | |
| 5,346,720 A | 9/1994 | Lombard et al. | |
| 5,451,920 A | 9/1995 | Hoffheins et al. | |
| 5,796,019 A * | 8/1998 | Lupton et al. | 75/235 |
| 6,139,777 A | 10/2000 | Omoya et al. | |
| 6,800,158 B2 | 10/2004 | Polikarpus et al. | |
| 2003/0111341 A1 | 6/2003 | Wiedenmann et al. | |
| 2004/0195093 A1 | 10/2004 | Cohen et al. | |

FOREIGN PATENT DOCUMENTS

| | | | |
|---|---|---|---|
| JP | 8 8044 | | 1/1996 |
| JP | 8-8044 | * | 1/1996 |
| JP | 2003-277801 | | 10/2003 |

OTHER PUBLICATIONS

Palladium property article gotten from website http://www.chemicalelements.com/elements/pd.html[Nov. 20, 2012 4:47:13 PM].*
Martin, et al. "Palladium and Palladium Alloy Electrodeposits in the Electronics Industry" Metal Finishing. pp. 39-41. Jan. 1990.
Rand, et al. "The Nature of Absorbed Oxygen on Rhodium, Palladium and Gold Electrodes" Electroanalytical Chemistry and Interfacial Electrochemistry.J.Electroanal. Che., 31 (1971) 29-38.
Kawashima, et al. "Surface-Activated Amorphous Alloy Fuel Electrodes for Methanol Fuel Cell" The 1761th report of the Research Institute for Iron, Steel and Other Metals.

(Continued)

*Primary Examiner* — J. Christopher Ball
*Assistant Examiner* — Jennifer Dieterle
(74) *Attorney, Agent, or Firm* — Mark H. Svoboda

(57) ABSTRACT

Disclosed herein is a method of making a sensing element comprising forming an electrically conductive element, wherein the sensing element comprises a metal selected from the group consisting of Pd and alloys and combinations comprising Pd; and wherein the electrically conductive element is thermally stable at temperatures as high as 1,200° C.

14 Claims, 6 Drawing Sheets

(56) References Cited

OTHER PUBLICATIONS

ASTM B527-93 (Reapproved 2000) "Standard Test Method for Determination of Tap Density of Metallic Powders and Compounds" pp. 1-2.

Nezu, S. and T. Sano. "Measurement of Hydrogen Loading Ratio of Pd Electrodes Cathodically Polarized in Aqueous Solutions" Fourth International Conference on Cold Fusion. 1983. Lahaina, Maui: Electric Power Research Institute 3412 Hillview Ave., Palo Alto, CA 94304. pp. 31-1 through 31-8.

* cited by examiner

SENSING ELEMENT AND METHOD OF MAKING THE SAME

CROSS-REFERENCE TO RELATED APPLICATION

This application is a divisional of prior application Ser. No. 11/281,056, filed Nov. 16, 2005.

TECHNICAL FIELD

The present disclosure is related to a sensing element and a method of making and, in particular, to a sensing element containing a palladium and/or palladium alloy electrically conductive element and a method of making the same.

BACKGROUND

Sensors, in particular gas sensors, have been utilized for many years in several industries (e.g., flues in factories, in furnaces and in other enclosures; in exhaust streams such as flues, exhaust conduits, and the like; and in other areas). For example, the automotive industry has used exhaust gas sensors in automotive vehicles to sense the composition of exhaust gases, namely, oxygen. A sensor may be used to determine the exhaust gas content for alteration and optimization of the air to fuel ratio for combustion.

One type of sensor employs an ionically conductive solid electrolyte between porous electrodes. For oxygen detection, solid electrolyte sensors are used to measure oxygen activity differences between an unknown gas sample and a known gas sample. In the application of a sensor for automotive exhaust, the unknown gas is exhaust and the known gas, i.e., reference gas, is usually atmospheric air because the oxygen content in air is relatively constant and readily accessible. This type of sensor is based on an electrochemical galvanic cell operating in a potentiometric mode to detect the relative amounts of oxygen present in an automobile engine's exhaust. When opposite surfaces of this galvanic cell are exposed to different oxygen partial pressures, an electromotive force (EMF) is developed between the electrodes according to the Nernst equation.

According to the Nernst principle, chemical energy is converted into electromotive force. Thus, a gas sensor based upon this principle typically consists of an ionically conductive solid electrolyte material, a porous electrode with a porous protective overcoat exposed to exhaust gases ("sensing electrode"), and a porous electrode exposed to the partial pressure of a known gas ("reference electrode"). Sensors used for automotive applications typically employ a yttria stabilized zirconia based electrochemical galvanic cell with porous platinum electrodes, operating in potentiometric mode, to detect the relative amounts of a particular gas, such as oxygen for example, that is present in an automobile engine's exhaust. Also, a typical sensor has a ceramic heater attached to help maintain the sensor's ionic conductivity at low exhaust temperatures. When opposite surfaces of the galvanic cell are exposed to different oxygen partial pressures, an electromotive force is developed between the electrodes on the opposite surfaces of the zirconia wall, according to the Nernst equation:

$$E = \left(\frac{-RT}{4F}\right)\ln\left(\frac{P_{O_2}^{ref}}{P_{O_2}}\right)$$

where:
E=electromotive force
R=universal gas constant
F=Faraday constant
T=absolute temperature of the gas
$P_{O_2}^{ref}$=oxygen partial pressure of the reference gas
$P_{O_2}$=oxygen partial pressure of the exhaust gas Due to the large difference in oxygen partial pressure between fuel rich and fuel lean exhaust conditions, the electromotive force (EMF) changes sharply at the stoichiometric point, giving rise to the characteristic switching behavior of these sensors. Consequently, these potentiometric oxygen sensors indicate qualitatively whether the engine is operating in fuel rich or fuel lean conditions, without quantifying the actual air to fuel ratio of the exhaust mixture.

In addition to oxygen, the exhaust gas contains many components including carbon monoxide, carbon dioxide, hydrogen, water, nitrogen oxides, nitrogen, and a variety of hydrocarbons and hydrocarbon derivatives. Because the exhaust gas is a non-equilibrium mixture containing products of incomplete combustion, the oxygen partial pressure is not an equilibrium pressure. Because the oxygen partial pressure is not at equilibrium, sensors do not operate at stoichiometric air to fuel ratios per the Nernst equation. In addition, the use of zirconia-based electrolyte materials contributes to non-ideal sensor behavior.

To provide a means of monitoring the cell potential and to circumvent at least some of the difficulties associated with non-equilibrium conditions, catalytic electrodes are used to both catalyze the oxidation reactions and to equilibrate the local oxygen concentrations. Ideal sensors produce a sharp EMF or voltage step at a stoichiometric air to fuel ratio per the Nernst equation. Manufactured sensors, however, exhibit non-ideal behaviors, for example, a broadened voltage transition that occurs over a range of air to fuel ratios near the stoichiometric ratio. In addition, the sensor EMF may depend upon mass transport processes, adsorption, desorption and chemical reactions that occur at the electrodes.

Platinum (Pt) is widely used as the material for various electrically conductive components of exhaust sensors such as, for example, electrodes, sensing elements, heaters, ground planes, leads, vias, contact pads, and the like. The use of Pt in exhaust sensors such as oxygen, nitrogen oxide and ammonia is desirable because it can withstand many process application temperatures without degradation due to its exceptional physical and chemical properties. However, the market price of Pt has historically been high, thereby increasing the cost of manufacturing sensors that use Pt.

Accordingly, a need exists in the sensor manufacturing art for less expensive methods and/or materials for producing such sensors.

SUMMARY

Disclosed herein is a sensing element comprising: an electrochemical cell; wherein the sensing element comprises a metal selected from the group consisting of Pd and alloys and combinations comprising at least one of the foregoing; and wherein the electrically conductive element is thermally stable at temperatures as high as 1,200° C.

Also disclosed herein is a method of making a sensing element, comprising: forming a precursor material comprising a plurality of non-spherically shaped Pd particles and an organic vehicle; disposing the precursor material on a supporting surface to define an electrically conductive element; and heating the precursor material to a temperature of greater than or equal to about 1450° C. for a sufficient period of time to sinter the precursor material and form the sensing element; wherein the electrically conductive element is thermally stable at a temperature of about 1,200° C.

The above described and other features are exemplified by the following figures and detailed description.

BRIEF DESCRIPTION OF THE DRAWINGS

Refer now to the figures, which are exemplary embodiments, and wherein like elements are numbered alike.

DESCRIPTION

At the outset of the description, it should be noted that the terms "first," "second," and the like, herein do not denote any order, quantity, or importance, but rather are used to distinguish one element from another, and the terms "a" and "an" herein do not denote a limitation of quantity, but rather denote the presence of at least one of the referenced items. The modifier "about" used in connection with a quantity is inclusive of the stated value and has the meaning dictated by the context (e.g., includes the degree of error associated with measurement of the particular quantity). It is noted that the terms "bottom" and "top" are used herein, unless otherwise noted, merely for convenience of description, and are not limited to any one position or spatial orientation. Furthermore, all ranges disclosed herein are inclusive and combinable (e.g., ranges of "up to about 25 weight percent (wt. %), with about 5 wt. % to about 20 wt. % desired, and about 10 wt. % to about 15 wt. % more desired," are inclusive of the endpoints and all intermediate values of the ranges, e.g., "about 5 wt. % to about 25 wt. %, about 5 wt. % to about 15 wt. %", etc.). Finally, unless defined otherwise, technical and scientific terms used herein have the same meaning as is commonly understood by one of skill in the art to which this invention belongs. The suffix "(s)" as used herein is intended to include both the singular and the plural of the term that it modifies, thereby including one or more of that term (e.g., the metal(s) includes one or more metals).

Disclosed herein is a sensing element comprising electrically conductive element(s) (e.g., ground plane(s), lead(s), via(s), contact pad(s), low conductance resistor(s) (e.g., a heater)) comprising palladium (Pd), e.g., comprising Pd in combination (e.g., solid solution, alloy, and/or mixture) with rhodium (Rh), iridium (Ir), and/or platinum (Pt), and combinations comprising at least one of the foregoing. These electrically conductive elements are thermally stable at temperatures comparable to and in some instances greater than the thermal stability of platinum, which is unexpected because Pd has a relatively low melting point. For example, the electrically conductive elements are thermally stable after sintering at a firing temperature of greater than or equal to about 1,400° C., e.g., temperatures of about 1,450° C. to about 1,530° C., which elements made from spherical Pd materials may not be capable of withstanding. Optionally, a metal oxide can be included in the electrically conductive element(s). In addition, the sheet resistivity of these electrically conductive element(s) can be controlled, e.g., can be varied by varying the concentration of the metal oxide, and/or of the Rh, Ir and/or Pt in the element.

Figure 1:
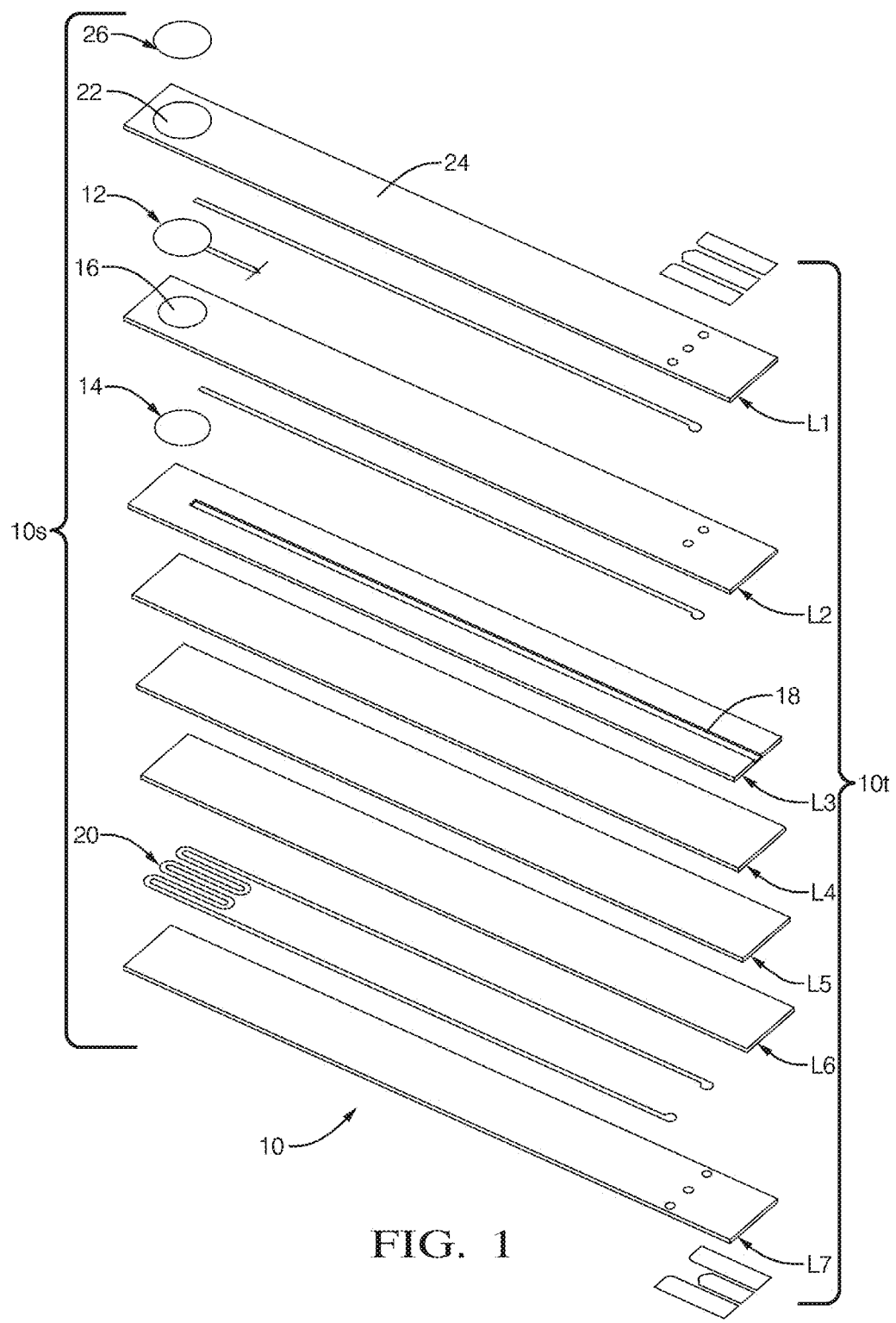
FIG. 1 is an expanded isometric view of an oxygen sensing element.

An exemplary planar oxygen-sensing element 10 is shown in FIG. 1. Although described herein in connection with an oxygen-sensing element, it is to be understood that the electrically conductive element(s) disclosed herein can be utilized in other types of sensors such as temperature sensors and gas sensors (e.g., nitrogen sensors, hydrogen sensors, hydrocarbon sensors, ammonia sensors, and the like). In addition, although described in connection with a planar sensing element, it is to be understood that the electrically conductive element(s) can be employed in other types of sensing elements such as, for example, wide-range, switch-type, conical, and the like.

As shown in FIG. 1, sensing element 10 can comprise a sensing end 10s and a terminal end 10t. The sensing element 10 can comprise a sensing (i.e., first, exhaust gas, or outer) electrode 12, a reference gas (i.e., second or inner) electrode 14, and an electrolyte portion 16. The electrolyte portion 16 can be disposed at the sensing end 10s with the electrodes 12, 14 disposed on opposite sides of, and in ionic contact with, the electrolyte portion 16, thereby creating an electrochemical cell (12/16/14).

A reference gas channel 18 can be disposed on the side of the reference electrode 14 opposite the electrolyte portion 16. The reference gas channel 18 can be disposed in fluid communication with the reference electrode 14 and with a reference gas (e.g., the ambient atmosphere, the exhaust gas, or another gas supply).

A heater 20 can be disposed on a side of the reference gas channel 18 opposite the reference electrode 14, for maintaining sensing element 10, and in particular, the sensing end 10s of the sensing element, at a desired operating temperature. The heater 20 can be any heater capable of maintaining the sensor end 10s at a sufficient temperature to facilitate the various electrochemical reactions therein. The heater 20 can be, for example, Pt, aluminum (Al), Pd, and the like, as well as oxides, mixtures, and alloys comprising at least one of the foregoing metals. Optionally, the heater can be one of the electrically conductive element(s). The heater 20 can be disposed on one of the support layers by various methods such as, for example, screen-printing. The thickness of the heater 20 can be about 5 micrometers to about 50 micrometers, or so.

A protective layer L1 can be disposed adjacent to the sensing electrode 12 opposite the electrolyte portion 16. The protective layer L1 can comprise a solid portion 24 and a porous portion 22 disposed adjacent to the sensing electrode 12. The porous portion 22 can be a material that enables fluid communication between the sensing electrode 12 and the gas to be sensed. For example, the porous portion 22 can comprise a porous ceramic material formed from a precursor comprising a ceramic (e.g., spinel, alumina, zirconia, and/or the like), a fugitive material (e.g., carbon black), and an organic binder. The fugitive material can provide pore formation in the fired layer. The porous portion 22 can be formed, for example, from a precursor comprising about 70 to about 80 weight percent (wt. %) of one or more of the foregoing ceramic materials, about 5 to about 10 wt. % of the fugitive material, and about 15 wt. % to about 20 wt. % of an organic binder, based upon the total weight of the precursor, which can be applied using various methods including thick film methods, and the like, followed by sintering.

In order to further protect the sensing electrode 12, a protective coating 26 can optionally be disposed over the porous portion 22 and optionally over layer L1. As with the porous portion 22, at least in the area of the porous portion 22, the protective coating 26 allows fluid communication between the sensing electrode 12 and the gas to be sensed. Possible materials for the protective coating 26 can comprise spinel, alumina (e.g., stabilized alumina), and other protective coatings employed in sensors.

If desired, one or more support layers can be disposed on a side of the sensing electrode 12 opposite the electrolyte 16; between the reference gas channel 18 and the heater 20, and on a side of the heater 20 opposite the reference gas channel 18. As shown, insulating layer L1 is disposed on a side of the sensing electrode 12 opposite the electrolyte portion 16; support layers L3-L6 are disposed between the reference electrode 14 and the heater 20; and support layer L7 is disposed on a side of the heater 20 opposite the reference gas channel 18. A support layer L2 can be employed with the electrolyte 16 disposed therethrough, attached to an end thereof, or the electrolyte can comprise the entire layer.

The support layers, e.g., L2-L7, that can provide structural integrity (e.g., protect various portions of the gas sensor from abrasion and/or vibration, and the like, and provide physical strength to the sensor); physically separate and electrically isolate various components; and provide support for various components that can be formed in or on the layers. Depending on the arrangement, the support layers can each comprise the same or different materials, e.g., a dielectric material (e.g., alumina ($Al_2O_3$)), an electrolytic material (e.g., zirconium oxide (zirconia)), protective material, and the like. Each of the support layers can comprise a thickness of up to about 500 micrometers so, depending upon the number of layers employed, or, more particularly, about 50 micrometers to about 200 micrometers. Although illustrated herein as comprising seven layers L1-L7, it should be understood that the number of layers could be varied depending on a variety of factors.

Electrolyte portion 16 can comprise a solid electrolyte. The electrolyte portion 16 can be disposed through layer L2 in a variety of arrangements. For example, the electrolyte portion 16 can be attached to L2 at the sensing end such that the electrolyte portion 16 forms the sensing end of L2, disposed in an aperture (not illustrated) adjacent to the sensing end 10s, and disposed in an opening through the layer L2. The latter arrangement eliminates the use of excess electrolyte. Any shape can be used for the electrolyte, with the size and geometry of the various inserts, and therefore the corresponding openings, being dependent upon the desired size and geometry of the adjacent electrodes. The openings, inserts, and electrodes can comprise a substantially compatible geometry such that sufficient exhaust gas access to the electrode(s) is enabled and sufficient ionic transfer through the electrolyte is established to attain the desired sensor function. The electrolyte can comprise a thickness of up to about 500 micrometers or so, more specifically, about 25 micrometers to about 500 micrometers, and even more specifically, about 50 micrometers to about 200 micrometers.

The electrolyte 16 can be, for example, any material that is capable of permitting the electrochemical transfer of oxygen ions while inhibiting the passage of exhaust gases, desirably has an ionic/total conductivity ratio of approximately unity, and is compatible with the environment in which the sensor will be utilized. Possible electrolyte materials can comprise any material capable of functioning as a sensor electrolyte including, but not limited to, zirconium oxide (zirconia), cerium oxide (ceria), calcium oxide, yttrium oxide (yttria), lanthanum oxide, magnesium oxide, ytterbium (III) oxide ($Yb_2O_3$), scandium oxide ($Sc_2O_3$), and so forth, as well as combinations comprising at least one of the foregoing. If zirconia is employed, it can be stabilized with, for example, with calcium, barium, yttrium, magnesium, aluminum, lanthanum, cesium, gadolinium, and so forth, as well as combinations comprising at least one of the foregoing materials. For example, the electrolyte can be alumina stabilized zirconia and/or yttrium stabilized zirconia.

Accordingly, formation of electrically conductive element(s) of the sensing element 10 can comprise preparing a suitable precursor material such as an ink, paste, slurry and/or the like. For example, a precursor (ink) can be formed by mixing a metal powder with a sufficient quantity of an organic vehicle to attain the desired adhesion to the substrate after firing, as well as other properties. It is noted that the Pd materials described herein can be used as the sensing electrode to sense hydrogen, but are not particularly sensitive to oxygen. Hence, although it is contemplated that the Pd materials can be employed to form the electrodes, they are generally employed only to form the other electrically conductive components (e.g., leads, heater, ground plane, vias, and so forth).

The metal powder can comprise a Pd that can optionally be combined with Rh, Ir, and/or Pt. The Pd powder preferably has a surface area of about 0.5 $m^2/g$ to about 5.0 $m^2/g$, more particularly, about 1.0 $m^2/g$ to about 4.0 $m^2/g$, and more particularly still, about 2.0 $m^2/g$ to about 3.0 $m^2/g$. The Pd powder also can comprise a particle size distribution at 90 percent (i.e., a P.S.D. 90) of about 1 micrometer to about 5 micrometers, and a tap density of about 0.5 grams per cubic centimeter ($g/cm^3$) to about 4.0 $g/cm^3$.

Optionally, the precursor material can comprise a metal oxide, for example, to improve the adhesion of the electrically conductive element(s) to underlying substrate (where applicable), and/or impart beneficial properties such as inhibition of further sintering. Possible metal oxides can comprise ceria, lanthana, magnesia, zirconia, yttria, alumina, scandia, and the like, and mixtures comprising at least one of the foregoing. The amount of metal oxide employed is dependent upon the particular metals employed and the temperatures used in forming the sensor. The amount of metal oxide can be up to about 25 wt %, based upon a total amount of solids in the precursor material. In some embodiments, the amount of metal oxide can be about 2 wt % to about 10 wt % (e.g., for a Pd material), while in other embodiments, the amount of metal oxide may be about 0.2 wt % to about 2 wt % (e.g., for a Pd—Rh material).

The metal powder and optional metal oxide can be combined with a vehicle (e.g., an organic vehicle) to enable deposition of the precursor onto the desired portion(s) of the sensor element.

Figure 2:
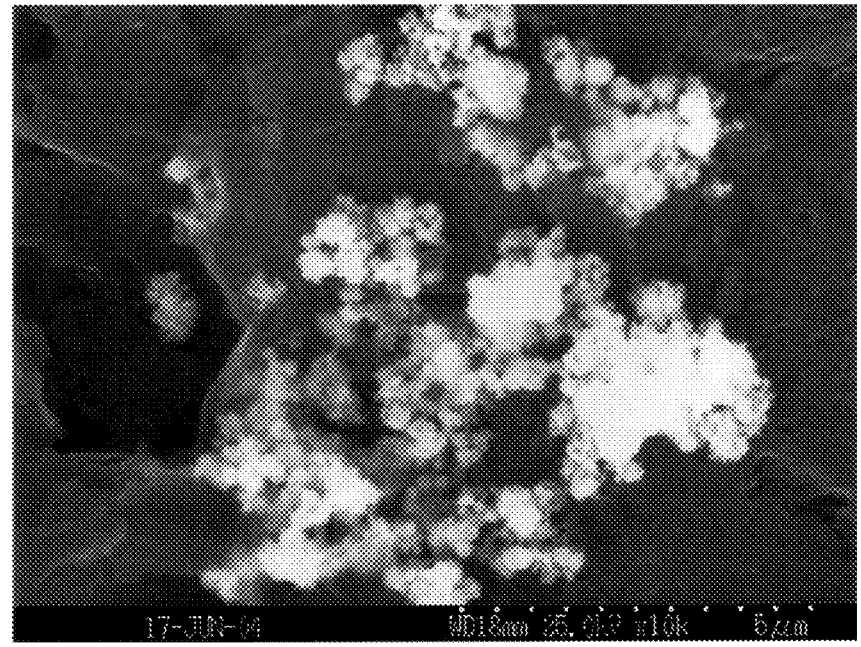
FIG. 2A shows a scanning electron microscope (SEM) image of a non-spherically shaped Pd powder.
FIG. 2B shows a SEM image of a spherically shaped, relatively high surface area Pd powder.
Figure 2:
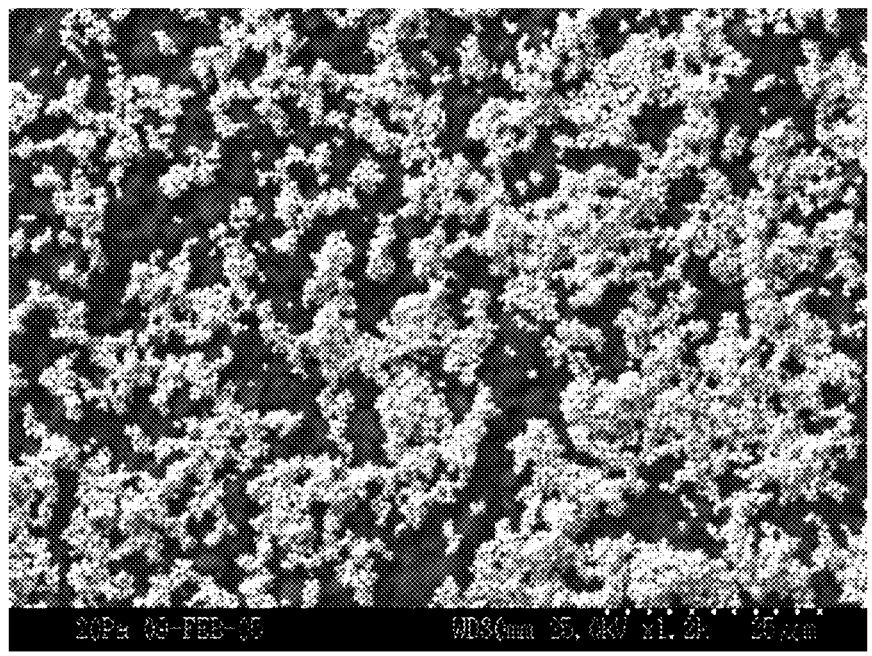

It has been discovered, unexpectedly, that electrically conductive element(s) formed from a relatively low surface area (e.g., less than or equal to about 5.0 m$^2$/g) and non-spherical shaped (e.g., a sponge or a flake) Pd powder (as shown in FIG. 2A), in comparison to those formed from spherically shaped Pd powder (as shown in FIG. 2B), can provide increased thermal stability. It should be understood that relatively high surface area powders have a spherical shape. Not to be bound by any theory, it is thought that the non-spherical shaped Pd particles can result in anisotropic densification of the thick film during high temperature firing (e.g., greater than or equal to about 1,450° C.), with in-plane densification being reduced. In contrast, it is thought that the spherically shaped Pd particles can yield isotropic densification of the thick film, with large three-dimensional shrinkages, which can cause electrically conductive element cracking and delamination of the electrically conductive element from the substrate during high temperature firing. Thus, the Pd powder can comprise a non-spherical shape, and the Rh, Pt and/or Ir powders can comprise either a non-spherical or a spherical shape.

After mixing the metal powder, the organic vehicle, and the optional metal oxide, the ink can comprise about 60 wt. % to about 70 wt. % solids and about 30 wt % to about 40 wt. % of the organic vehicle. The ink can comprise less than or equal to about 20 wt. % of each of the Rh, Ir, and/or Pt, more particularly about 0.5 wt. % to about 15 wt. %, and more particularly still about 2 wt % to about 10 wt %, based on the total weight of the metals in the precursor, with the balance comprising Pd. The precursor can comprise about 0.5 wt. % to about 25 wt. % metal oxide, based on the total concentration of solids in the precursor, more particularly about 0.5 wt. % to about 20 wt. %, and more particularly still, about 0.7 wt. % to about 18 wt. %.

Once prepared, the conductive element precursor material can be applied to the desired area of the sensor, using various application technique(s) such as thick film technique(s) including screen printing, painting, spraying, dipping, coating, and the like. Depending upon the particular electrically conductive element, as well as the particular technique employed, optional thickener(s), binder(s), additive(s), fugitive material(s) (e.g., carbon, insoluble organic material, and the like), and so forth (hereinafter additive(s)), can be employed in the precursor material in an amount of less than or equal to about 40 wt. % additives for screen printing, less than or equal to about 60 wt. % additives for pad flexing (painting), less than or equal to about 75 wt. % additives for spray coatings, less than or equal to about 90 wt. % additives for dip coatings, based on the total weight of thick film inks. Possible additives include: 1-ethoxypropan-2-ol, turpentine, squeegee medium, 1-methoxy-2-propanol acetate, butyl acetate, dibutyl phthalate, fatty acids, acrylic resin, ethyl cellulose, pine oil, 3-hydroxy, 2,2,4-trimethylpentyl isobutyrate, terpineol, butyl carbitol acetate, cetyl alcohol, cellulose ethylether resin, and so forth, as well as combinations comprising at least one of the foregoing.

The thickness of the electrically conductive elements (e.g., the leads, the heater, the ground plane, the contact pads, temperature sensor, the vias, and other electrically conductive components) is dependent upon the particular element. The thickness can be up to the thickness of the layer or so (e.g., for a via), or, more particularly, about 1 micrometers (μm) to about 50 micrometers, or, even more particularly, about 3 micrometers to about 35 micrometers, and still more particularly about 7 micrometers to about 25 micrometers.

Furthermore, the element precursor material can be applied during any point during the manufacturing process; i.e., before the substrate is fired (green), before the substrate is fully fired (bisque), or after the substrate is fully fired. In each case, once the element precursor material has been applied, the substrate is heated to a temperature sufficient to sinter the precursor material (e.g., greater than or equal to about 1450° C. for about 2 hours). Optionally, the electrically conductive elements can be co-fired with green layers (alumina ($Al_2O_3$), zirconia ($ZrO_2$), and so forth). For a coating comprising a metal oxide such as zirconia, alumina, for example, temperatures of about 1,400° C. or greater can be employed.

The foregoing sensor, and others comprising more or less cells, can be formed using a variety of methods in which the components can be formed and fired separately or formed (optionally laminated), and co-fired. For example, an electrolyte tape can be formed and partially fired to the bisque state. The precursor material can be prepared as described above and deposited on the appropriate portions of the support layer(s) and/or the electrolyte tape and connecting electrical leads to the ink. A protective layer and support layer(s) can be disposed accordingly, with a ground plane, temperature sensor, and/or heater disposed therein as desired. The lay-up can then be heated to a sufficient temperature to volatilize the organics and to sinter the metals in the precursor, thereby forming the sensor.

In one embodiment, during use, the sensor can be disposed in a fluid to be sensed, e.g., an exhaust stream. Based upon the condition of the fluid to be sensed, i.e. rich or lean, oxygen can be pumped in or out of the sensor by the pumping cell. The increase/decrease, accordingly, creates an oxygen partial pressure difference between the oxygen at the sensing electrode and at the reference electrode, thereby developing an electromotive force that can be correlated with the oxygen concentration.

The following examples are merely to further illustrate the sensor element, and/or the electrically conductive element(s), and are not intended to limit the scope thereof.

EXAMPLES

Example 1

Effect of the Surface Area of the Pd Powder

Electrically conductive layers were formed from Pd powder and 8 wt % alumina (based upon the total weight of the solids), and were fired at a temperature of about 1,530° C.

Figure 3:
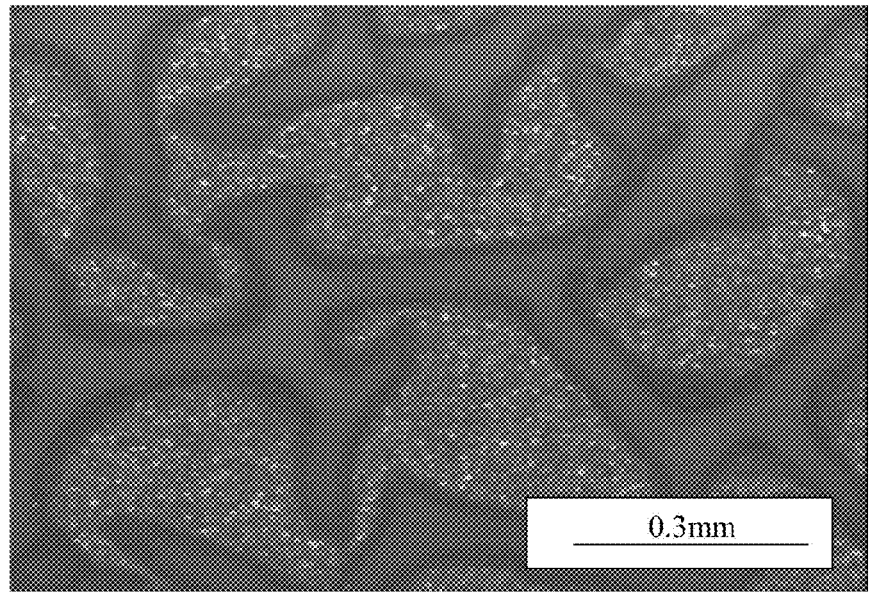
FIG. 3A is a copy of an optical micrograph showing cracks and delamination in a Pd thick film electrically conductive element formed from a relatively high surface area Pd powder, after firing at about 1,530° C.
FIG. 3B is a copy of an optical micrograph showing a Pd thick film electrically conductive element formed from a relatively low surface area Pd powder, after firing at about 1,530° C.
Figure 3:
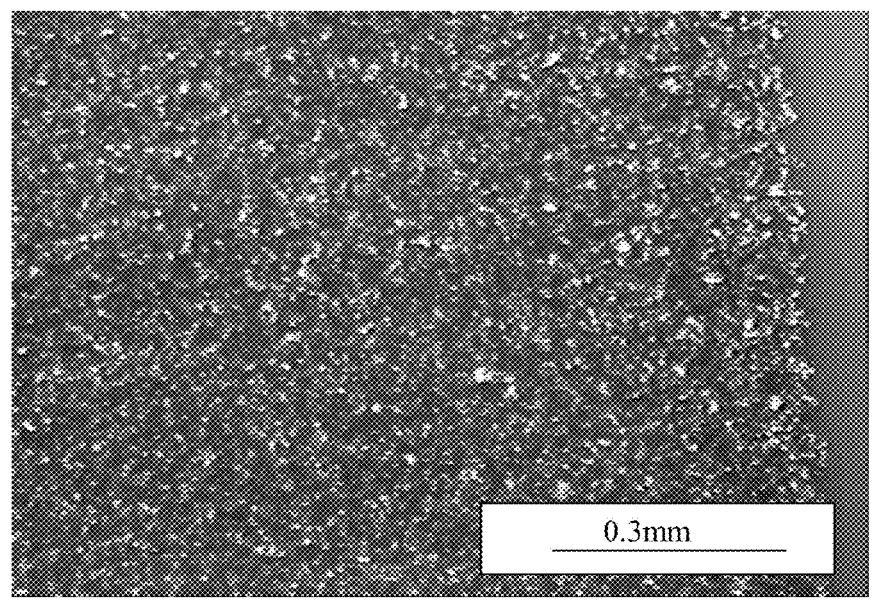

FIG. 3A shows an optical micrograph of a Pd electrically conductive layer formed from a relatively high surface area (13.5 square meters per gram ($m^2$/g)) Pd powder, after firing at 1,530° C. for 2 hours. As shown, the surface of the electrically conductive layer was cracked and portions were delaminated.

FIG. 3B shows an optical micrograph of a Pd electrically conductive layer formed from a relatively low surface area (1.9 $m^2$/g) Pd powder having a non-spherical shape, after firing at 1,530° C. for 2 hours. As shown, the surface of the electrically conductive layer was continuous and uniform, and the adhesion of the electrically conductive layer to the ceramic substrate was maintained.

The results show that the physical properties of the Pd powder used in the ink determine, at least in part, the electrically conductive layer morphology after firing. The use of low surface area, non-spherically shaped Pd powder can be advantageous for relatively high temperature firing applications (e.g., greater than 1,400° C.).

Example 2

Effect of the Physical Properties of the Pd Powder in Pd Alloys

Electrically conductive layers were formed using 5 wt. % Rh, and 0.7 wt. % alumina, balance Pd. Various Pd powders were used. All of the electrically conductive layers were fired at a temperature of about 1,530° C. for 2 hours.

Figure 4:
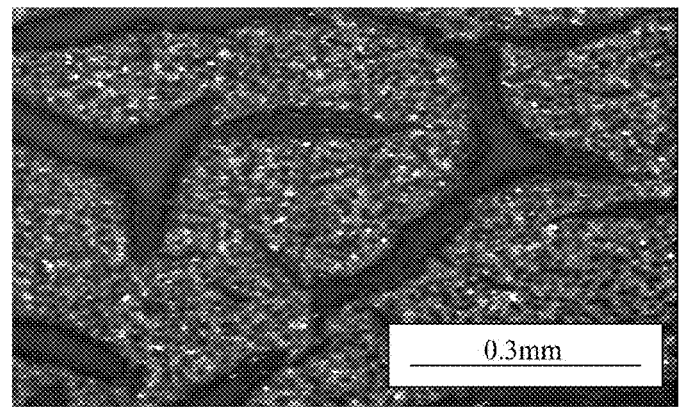
FIG. 4A is a copy of an optical micrograph of a Pd—Rh alloy thick film electrically conductive element formed from a relatively high surface area Pd powder, after firing at about 1,530° C.
FIG. 4B is a copy of an optical micrograph of a Pd—Rh alloy thick film electrically conductive element formed from a relatively low surface area Pd powder with spherically shaped particles, after firing at about 1,530° C.
FIG. 4C is a copy of an optical micrograph of a Pd—Rh alloy thick film electrically conductive element formed from a relatively low surface area Pd powder with non-spherically shaped particles, after firing at about 1,530° C.
Figure 4:
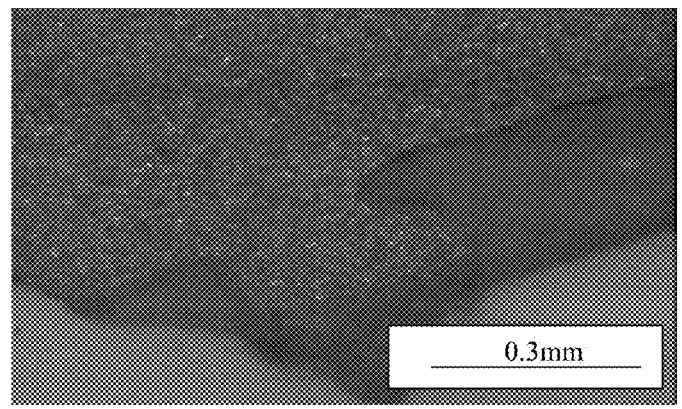
Figure 4:
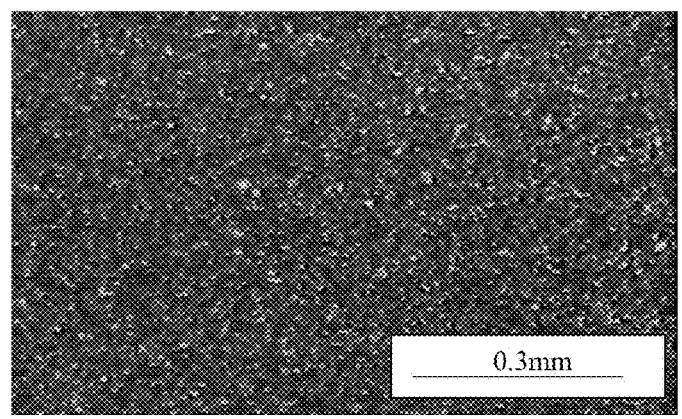

FIG. 4A shows an optical micrograph of a Pd—Rh alloy electrically conductive layer formed from the relatively high surface area (12.8 m$^2$/g) Pd powder. FIG. 4B shows an optical micrograph of a Pd—Rh alloy electrically conductive layer formed from the relatively low surface area (1.9 m$^2$/g) Pd powder having spherically shaped particles. FIG. 4C shows an optical micrograph of a Pd—Rh alloy electrically conductive layer formed from a relatively low surface area (1.9 m$^2$/g) Pd powder having a non-spherical shape, after firing at 1,530° C. The result show that the physical property of the Pd powder in Pd—Rh electrically conductive layers were similar to the non-alloyed Pd electrically conductive layers illustrated in FIGS. 3A and 3B. The Pd—Rh electrically conductive layers formed from relatively low surface area, non-spherically shaped Pd powder provided a continuous, uniform, crack-free, lift-free electrically conductive layer.

In addition, the adhesion of the Pd—Rh electrically conductive layer formed from relatively low surface area, non-spherically shaped Pd powder was comparable to that of the pure Pd electrically conductive layer formed from relatively low surface area, non-spherically shaped Pd powder. The results show that the electrically conductive layers formed from the Pd—Rh formed from relatively low surface area, non-spherically shaped Pd powder have good adhesion and morphology with lower oxide loading (e.g., 0.7 wt %), which is advantageous in some instances because the resistivity of the electrically conductive layer increases with the concentration of metal oxide. Not to be bound by any theory, it is believed that various finely dispersed Pd—Rh internal oxides (e.g., oxides formed as part of a Pd and Rh solid solution) were formed during firing, which promoted adhesion between the electrically conductive layer and substrate, and reduced the loading requirement of oxides in the precursor.

Example 3

Sheet Resistivity of Pd—Rh Electrically Conductive Layers

A Veeco FPP-100 four-point probe instrument was used to measure the sheet resistivity of fired Pd—Rh alloy electrically conductive layers. It should be recognized that the firing temperature for all of the samples listed in Table 1 was targeted to be about 1,500° C., and the range of actual temperatures from 1,493° C. to 1,508° C. achieved is not considered a significant variation for the firing process. The sheet resistivity of a standard Pt electrically conductive layer was used as a reference, as shown below in Table 1.

TABLE 1

| Sample | Electrically conductive layer composition after firing (wt. %) | | | | Firing Temperature (°C.) | Sheet Resistivity (×10$^{-3}$ μΩ·cm) |
|---|---|---|---|---|---|---|
| | Pt | Pd | Rh | Metal Oxide | | |
| A | 92.0 | N/A | N/A | 8.0 | 1,508 | 6.7 |
| B | N/A | 96.3 | 3.0 | 0.7 | 1,504 | 3 |
| C | N/A | 94.3 | 5.0 | 0.7 | 1,505 | 4.8 |
| D | N/A | 89.4 | 9.9 | 0.7 | 1,505 | 10.5 |
| E | N/A | 84.4 | 14.9 | 0.7 | 1,493 | 12 |

μΩ · cm = micro Ohm · centimeter

As shown in Table 1, sheet resistivity values for the Pd—Rh alloy electrically conductive layers were above or below that of the Pt electrically conductive layer (A), based on the concentration of the Rh and/or the metal oxide. Although Pd containing electrically conductive layers can have a sheet resistivity of up to 15×10$^{-3}$ μΩ·cm, sheet resistivities of less than or equal to about 12.0×10$^{-3}$ μΩ·cm, or, more specifically, less than or equal to about 6×10$^{-3}$ μΩ·cm, or, even more specifically, less than or equal to about 4×10$^{-3}$ μΩ·cm, and even more specifically, less than or equal to about 3×10$^{-3}$ μΩ·cm are achievable.

The results show that the Pd and Pd containing materials (e.g., Pd—Rh solid solution, alloy, so forth) thick film inks can be used to form both conductors such as ground, leads, vias, and contact pads, as well as resistors of controlled, lower conductance, such as heaters in sensor applications, each of which has a different requirement for electrical resistivity. For example, leads and vias require low resistance to minimize energy loss. Therefore, Samples (B) and (C) were good candidates for forming applications such as leads and vias in sensor elements. In contrast, the requirement for a ground plane is less strict; a ground plane electrically conductive layer can have marginal electrical conductivity after firing. Therefore, Samples (D) and (E) were good candidates for forming ground planes. Heaters can have high resistance in order to generate power. Therefore, by adjusting the electrically conductive layer thickness, all of the foregoing compositions can be used to make heaters.

Example 4

Weight Change of Exposed Electrically Conductive Layers as a Function of Temperature The change in weight of an electrically conductive layer material is an indicator of its thermal stability: a weight gain can indicate that the electrically conductive layer has been oxidized, and a weight loss can indicate that an oxide has been decomposed and that some material has been volatilized. The relative measure of weight change (gain or loss) is considered a measure of the thermal stability of the electrically conductive layer.

Figure 5:
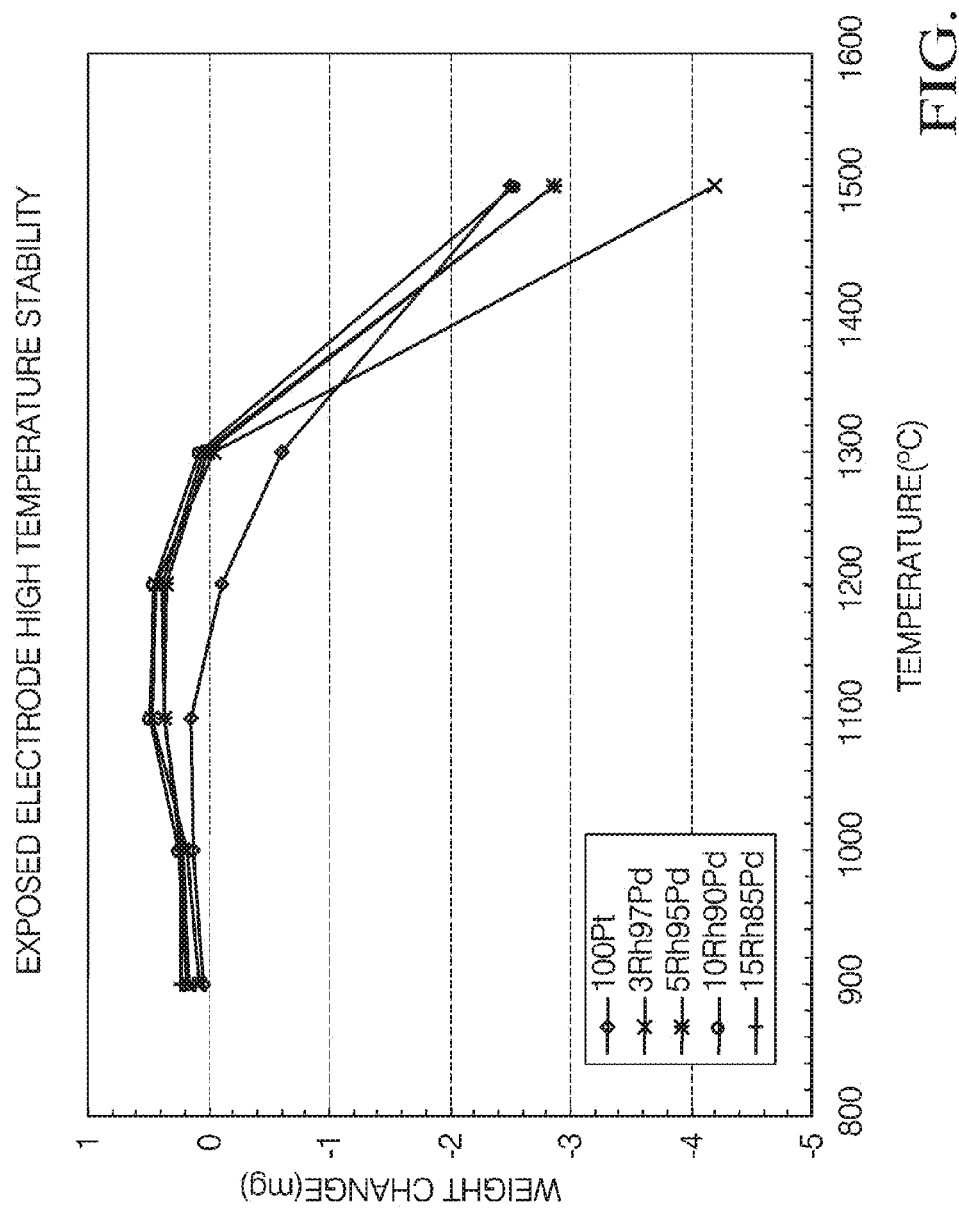
FIG. 5 is a graphical representation of the thermal stability of exposed Pd—Rh alloy electrically conductive elements as a function of rhodium (Rh) concentration.

FIG. 5 is a graphical representation of the weight change of various exposed electrically conductive layers (e.g., Pd—Rh alloys vs Pt) as a function of temperature, wherein the numbers represent the weight percent of each component (e.g., 3Rh97Pd is 3 wt % Rh and 97 wt % Pd). As shown, all of the electrically conductive layer compositions showed a reduction in weight at temperatures of greater than or equal to about 1,200° C. As shown in FIG. 5, the weight change of the Pd—Rh alloy electrically conductive layers was comparable to that of the Pt electrically conductive layers in an exposed environment at temperatures below about 1,100° C. At temperatures of greater than or equal to about 1,100° C., the Pd—Rh alloy electrically conductive layers showed some weight gain, e.g., due to oxidation, whereas the weight of the Pt electrically conductive layer remained unchanged. At a temperature of about 1,350° C., both the Pd—Rh alloy electrically conductive layers and the Pt electrically conductive layer showed a decrease in weight, e.g., as a result of metal volatilization.

Thus, the thermal stability of exposed Pd—Rh electrically conductive layers was comparable to the Pt electrically conductive layer at temperatures less than or equal to about 1,100° C. In addition, increasing the concentration of Rh in the Pd—Rh alloy electrically conductive layers increased the thermal stability of the Pd—Rh alloy electrically conductive layers at high temperature.

Example 5

Thermal Stability of Embedded Electrically Conductive Layers

In an exhaust sensor application, the electrically conductive layers are mostly embedded. The weight change as a function of temperature was compared for embedded electrically conductive layers having the same compositions as those used in Example 4. The Pt electrically conductive layer contained about 8 wt. % metal oxide.

Figure 6:
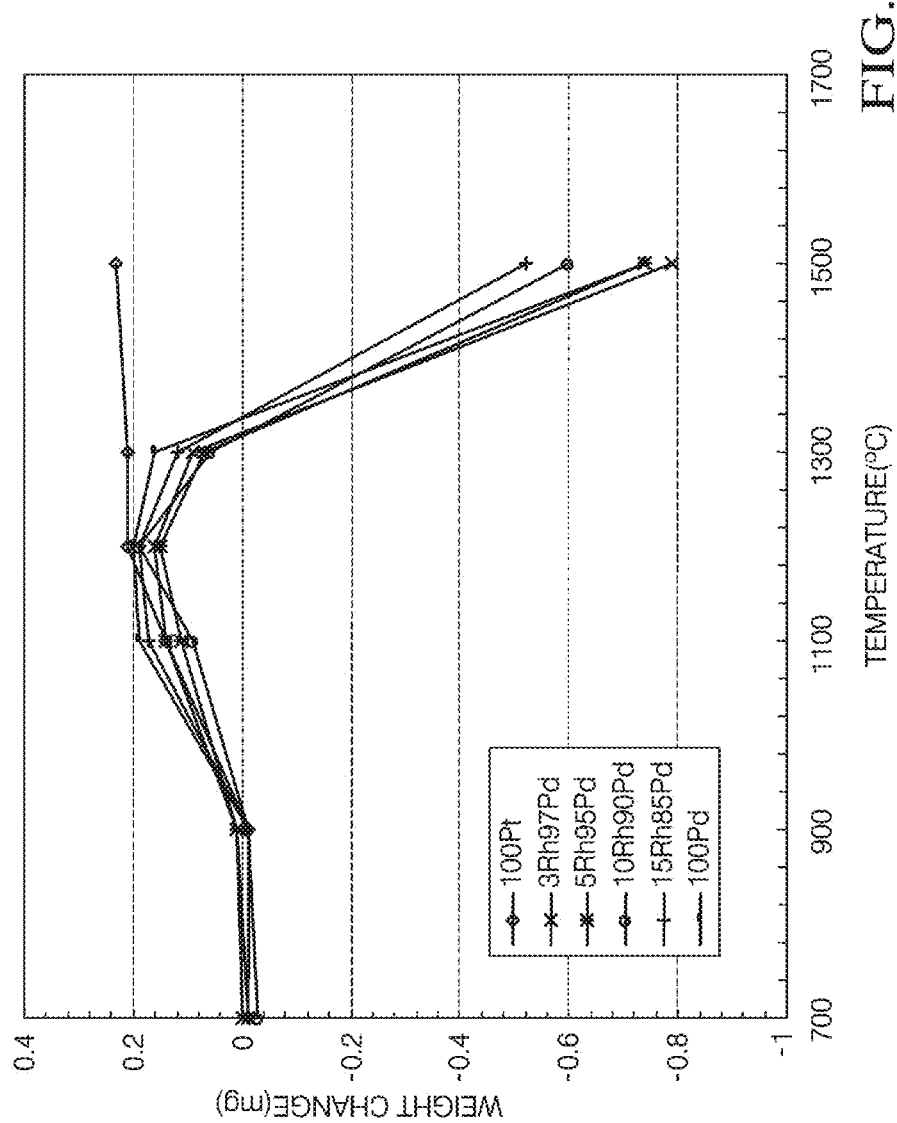
FIG. 6 is a graphical representation of the thermal stability of embedded Pd—Rh alloy electrically conductive elements as a function of rhodium (Rh) concentration.

FIG. 6 is a graphical representation of the weight change of the embedded electrically conductive layers as a function of temperature. As shown in FIG. 6, the weight change of the Pd—Rh electrically conductive layers was comparable to the Pt electrically conductive layer at temperatures of less than or equal to about 900° C. At temperatures of about 900° C. to about 1,200° C., the weight of all of the electrically conductive layers increased, e.g., due to high temperature oxidization. At temperatures greater than 1,300° C., the Pd—Rh electrically conductive layers showed a reduction in weight, whereas the weight of the Pt electrically conductive layer remained relatively stable. However, as is shown by the scale employed, the reduction in weight was not significant. Embedded Pd—Rh electrically conductive layers were thermally stable at a temperature of up to about 1,300° C. Additionally, Pd containing electrically conductive elements are stable at temperatures of 700° C. to 900° C. (i.e., temperatures at which sensors are often employed).

In summary, the Pd and Pd containing electrically conductive element ink compositions: 1) can be printed using thick film techniques; 2) can provide a lower sheet resistivity after sintering than Pt electrically conductive elements, allowing them to be used as leads (e.g., as shown in Example 2); 3) can be used for various electrically conductive elements such as heaters, leads, ground planes, vias, contact pads, and so forth; 4) can provide thermal stability after sintering at use temperatures as high as 1,200° C., in both exposed and embedded environments; 5) can provide thermal stability after sintering, especially in embedded environments; 6) can provide a significant cost reduction in comparison to other electrically conductive element materials such as Pt electrically conductive elements; 7) can provide good sintered adhesion to an underlying substrate (as is evident from the ability to bond to the substrate with lower and no metal oxide loading); 8) can be used to replace any of the electrically conductive elements other than sensing and reference electrically conductive elements 12 and 14 without compromising the physical, chemical and electric functionality of the sensor; thereby reducing costs.

While preferred embodiments have been shown and described, various modifications and substitutions may be made thereto without departing from the spirit and scope of the invention. Accordingly, it is to be understood that the present invention has been described by way of illustration only, and such illustrations and embodiments as have been disclosed herein are not to be construed as limiting to the claims.

What is claimed is:

1. A method of making a sensing element, comprising:
disposing a sensing electrode and a reference electrode in physical contact with an electrolyte;
disposing a precursor material on a supporting surface, the precursor material comprising a Pd powder that consists essentially of non-spherically shaped Pd particles having a surface area of about 0.5 m$^2$/g to about 5.0 m$^2$/g, to define an electrically conductive element; and
heating the precursor material to a temperature of greater than or equal to about 1,450° C. for a sufficient period of time to sinter the electrically conductive element and form the sensing element.

2. The method of claim 1, wherein the precursor material comprises sufficient Pd such that the electrically conductive element comprises greater than or equal to about 50 wt% of Pd, based upon the total weight of the sintered electrically conductive element.

3. The method of claim 1, wherein the precursor material comprises sufficient amount of a metal oxide such that the electrically conductive element comprises about 0.5 wt% to about 25 wt% of the metal oxide, based upon the total weight of the sintered electrically conductive element.

4. The method of claim 3, wherein the metal oxide is selected from the group consisting of zirconia, yttria, alumina, lanthana, ceria, magnesia, scandia, and combinations comprising at least one of the foregoing.

5. The method of claim 1, wherein the sintered electrically conductive element has a sheet resistivity of less than or equal to about 6×10$^{-3}$ μΩ·cm.

6. The method of claim 5, wherein the sheet resistivity is less than or equal to about 4×10$^{-3}$ μΩ·cm.

7. The method of claim 6, wherein the sheet resistivity is less than or equal to about 3×10$^{-3}$ μΩ·cm.

8. The method of claim 1, wherein the sintered electrically conductive element is thermally stable at temperatures as high as 1,200° C.

9. The method of claim 1, wherein the surface area is about 1.0 m$^2$/g to about 4.0 m$^2$/g.

10. The method of claim 9, wherein the surface area is about 2.0 m$^2$/g to about 3.0 m$^2$/g.

11. The method of claim 1, wherein the precursor material comprises sufficient amount of a metal selected from the group consisting of Pt, Rh, Ir, as well as combinations comprising at least one of the foregoing metals, such that the electrically conductive element further comprises about 0.25 wt% to about 20 wt% of the metal based upon the total weight of the sintered electrically conductive element.

12. The method of claim 11, wherein the electrically conductive element comprises about 0.25 wt% to about 10 wt% of the metal based upon the total weight of the sintered electrically conductive element.

13. The method of claim 11, wherein the metal is Rh.

14. The method of claim 11, wherein the metal and the Pd are a solid solution in the sintered electrically conductive element.

* * * * *